US009066937B2

(12) United States Patent
Vogt et al.

(10) Patent No.: US 9,066,937 B2
(45) Date of Patent: Jun. 30, 2015

(54) LIPOXYGENASE AND ITS USE IN WOUND HEALING

(75) Inventors: Peter Vogt, Hannover (DE); Bjoern Menger, Bovenden (DE); Kerstin Reimers-Fadhlaoui, Hannover (DE)

(73) Assignee: Medizinische Hochschule Hannover, Hannover (DE)

( * ) Notice: Subject to any disclaimer, the term of this patent is extended or adjusted under 35 U.S.C. 154(b) by 310 days.

(21) Appl. No.: 13/321,255

(22) PCT Filed: May 28, 2010

(86) PCT No.: PCT/EP2010/003254
§ 371 (c)(1),
(2), (4) Date: Nov. 18, 2011

(87) PCT Pub. No.: WO2010/136212
PCT Pub. Date: Dec. 2, 2010

(65) Prior Publication Data
US 2012/0148657 A1 Jun. 14, 2012

(30) Foreign Application Priority Data
May 29, 2009 (EP) .................................... 09007190

(51) Int. Cl.
| | | |
|---|---|---|
| *A61K 38/00* | (2006.01) | |
| *A61K 38/44* | (2006.01) | |
| *A61L 15/32* | (2006.01) | |
| *A61L 26/00* | (2006.01) | |
| *A61L 27/22* | (2006.01) | |
| *A61L 27/38* | (2006.01) | |
| *A61L 27/60* | (2006.01) | |
| *C12N 9/02* | (2006.01) | |

(52) U.S. Cl.
CPC ................. *A61K 38/44* (2013.01); *A61L 15/32* (2013.01); *A61L 26/0047* (2013.01); *A61L 27/227* (2013.01); *A61L 27/3813* (2013.01); *A61L 27/3834* (2013.01); *A61L 27/3895* (2013.01); *A61L 27/60* (2013.01); *C12N 9/0069* (2013.01); *G01N 2333/90241* (2013.01); *G01N 2500/04* (2013.01)

(58) Field of Classification Search
CPC ............... C12Y 113/11031; C12Y 113/11033; C12Y 113/1104; C12Y 113/11045; C12Y 101/00; C12Y 113/11012
USPC .......................................... 424/94.4; 435/189
See application file for complete search history.

(56) References Cited

U.S. PATENT DOCUMENTS 6,204,037 B1 * 3/2001 Brash et al. .................... 435/189

FOREIGN PATENT DOCUMENTS

WO WO 2004/060274 7/2004

OTHER PUBLICATIONS

SEQ ID No. 2 and B5A597 (Sep. 23, 2008).*
SEQ ID No. 1 and EU814616 (Jul. 16, 2008).*
Database Medline(online) US National Library of Medicine (NLM), Bethesda, Md. US. Jun. 2010, Menger., B., et al., "Lessons from the Mexican axolotl: amphibian limb regeneration and its impact on plastic surgery," XP009138275 Database accession No. NLM20517075 & Plastic and Reconstructive Surgery Jun. 2010 LNKD-PUBMED:20517075, vol. 125, No. 6, Jun. 2010, pp. 260-1e, ISSN:1529-4242.
Roy, S., et al., "Limb Regeneration in Axolotl: is it superhealing?", The ScientificWorld Journal, 6(s1), (2006) pp. 12-25—XP009138335.
Krieg, P., et al. "A Gene Cluster Encoding Human Epidermis-type Lipoxygenases at Chromosome 17p13.1: Cloning, Physical Mapping, and Expression", Genomics, 73, (2001), pp. 323-330. XP-009138276—p. 2 of 2 (Sep. 2010).
Gronertt, K., et al., "A Role for the Mouse 12/15-Lipoxygenase Pathway in Promoting Epithelial Wound Healing and Host Defense", The Journal of Biological Chemistry, vol. 280, No. 15, (Apr. 2005), pp. 15267-15278—XP002599817.
BAPRAS, Dec. 2-4, 2009 Meeting—3 pages.
Plastische Chirurgie—Abstracts—Supplement 1, Sep. 2008 (2 pages).

* cited by examiner

*Primary Examiner* — Tekchand Saidha
(74) *Attorney, Agent, or Firm* — Whitham Curtis Christofferson & Cook, PC

(57) ABSTRACT

Epidermal lipoxygenase obtained from axolotl is utilized in pharmaceutical or cosmetic compositions. The compositions have use in wound healing, bone healing or conditioning of injured tissue, e.g. in wound dressings.

7 Claims, 4 Drawing Sheets

AmbLOXe - expressing cells

HumLOXe - expressing cells

LIPOXYGENASE AND ITS USE IN WOUND HEALING

In general, the present invention relates to epidermal lipoxygenase obtained from axolotl and pharmaceutical compositions containing the same. In particular, in a first aspect the present invention relates to pharmaceutical compositions containing lipoxygenase obtained from axolotl or functional homologues thereof having a lipoxygenase activity, in particular for use in wound healing, bone healing or conditioning of injured tissue, e.g. in wound dressings. In a further aspect, the present inventions relates to cosmetical compositions containing said lipoxygenase. Finally, the present invention provides methods for identifying modulators of wound healing, scarring, etc. comprising the step of determining compounds able to alterate the lipoxygenase enzyme activity.

PRIOR ART

Wound healing of skin, vessels, bones etc. are essential for surviving in nature. While in humans the regenerative possibilities are limited, e.g. in urodela amphibian the potential of regeneration is higher. The axolotl *Ambystoma mexicanum* of the genus *Ambystoma*, is well-known for their ability to regenerate most body parts. That is, among the higher vertebrates, the ability to re-grow e.g. amputated limbs as adults is restricted to urodela amphibians, like the Mexican axolotl. Although the phenomenon has been described in the 18$^{th}$ century, the underlying molecular mechanisms remain widely unknown. Regenerative success depends on the establishment of an inductive wound epithel and dedifferentiation of local cells in a regeneration blastema in a process called epimorphic regeneration. The reciprocal communication between inductive wound epidermis and blastema is widely unknown on molecular basis. Comparative evolutionary studies with experimental data suggest that the necessary pathways allowing epimorphic regeneration are still present in mammal cells, however, not developed in animals other than urodela amphibians.

Wound healing or wound repairs are an intricate process in which tissue like skin or other organs repairs itself after injury. For example, in normal skin the epidermis as the outermost layer and the dermis, the inner or deeper layer, exists in a steady stated equilibrium, forming a protective barrier against the external environment. Once the protective barrier is broken, the physiological process of wound healing or wound repairing starts immediately. Typically, the classic model of wound healing can be divided into several phases, namely: inflammatory phase, proliferative phase and remodelling.

In the inflammatory phase, debris and foreign material which may be present in the wound are phagocytized and removed. In addition, factors are released from the environment that causes the migration and division of local cells involved in the proliferative phase.

In the second phase, the proliferative phase, which may overlap with the first phase, angiogenesis, collagen deposition, fibroblasia, granulation tissue formation, epithelialisation and wound contraction occurs. In angiogenesis, new blood vessels grow from endothelial cells while in fibroblasia and granulation tissue formation, fibroblasts grow and form a new provisional extracellular matrix by excreting collagen and fibronectin. During epithelisation, epithelial cells grow across the wound bed to cover it. In contraction, the wound is made smaller by the action of myofibroblasts which establish the grip on the wound address and contract themselves.

However, this complex process is also very fragile. Any disturbance during the various phases of wound healing may result in abnormalities of said healing. For example, the formation of chronic non-healing wounds occur or, on the contrary, there is an excess of new tissue resulting in hypertrophic scaring or other defects in wound closure, such as keloid scar.

Today, there are a number of possibilities for wound management. However, a lot of parameters influence wound management which may eventually results in cicatrice or fibrosis.

In contrast, regeneration of tissue, namely new formation of tissue is a rare event. For example, regeneration of tissues is known from the urodela amphibians, like the Mexican axolotl. Regeneration includes the ability to newly build up complex organ structures or to re-grow new limbs. This type of regeneration requires dedifferentiation of cells in the area of amputation, proliferation of said cells and redifferentiation to build up the new limb. For example, in case of axolotl, after amputation of a limb, a condensed region in the area of the wound epithel occurs named apical-epithelial-cap (AEC) which is required for the progress of regeneration. The AEC develops into the blastema which represents the origin of the newly developed limb. It is noteworthy that in case the blastema is transplanted into another region, new formation of the limb occurs in the area of incorporation.

There is an ongoing demand in the art to understand the process of regeneration and wound healing allowing to provide new means for enabling and improving wound healing while limiting defects of the complex wound healing system.

BRIEF DESCRIPTION OF THE PRESENT INVENTION

The present inventors found that lipoxygenase represents a powerful tool for e.g. wound healing. In particular, lipoxygenase obtained from urodela amphibian like the axolotl are suitable for wound healing.

Thus, in the first aspect, the present invention relates to a pharmaceutical composition containing a polypeptide of SEQ ID No. 2 having a lipoxygenase enzyme activity or functional homologues thereof having a sequence in a similarity of at least 50% to the sequence of SEQ ID No. 2 maintaining the lipoxygenase enzyme activity, or nucleic acids encoding said polypeptide. The present inventors found that the lipoxygenase obtained from axolotl (SEQ ID Nos. 1 and 2) can influence and modulate wound healing. The lipoxygenase obtained from axolotl demonstrates superior properties in wound healing, thus, enabling its use in wound dressings or other forms for topical application.

For example, said lipoxygenase enzyme allows conditioning of scars or injured tissue and influencing wound healing, or bone healing like non-healing fractures, in particular chronic wound healing defects. In addition, it is possible to treat excessive scarring, like keloid or excessive scarring occurring in vessels, for example after myocardial infarction. Moreover, psoriasis or similar diseases may be treated.

In a further aspect, the present invention relates to cosmetical compositions containing said polypeptides or nucleic acid molecules.

In a further aspect, the present inventions relates to the use of said polypeptide having lipoxygenase enzyme activity or nucleic acids encoding the same for the in vitro generation of artificial tissue, in particular skin. The lipoxygenase enzymes are particularly useful for the in vitro generation of artificial tissue, in particular skin, for example used as transplants for individuals having burns.

Moreover, the present invention relates to methods for identifying modulators of wound healing, scarring, etc. comprising the step of determining the ability of a candidate agent to alter the activity of the polypeptide having lipoxygenase enzyme activity according to the present invention.

BRIEF DESCRIPTION OF THE DRAWINGS

FIG. 2 shows the effect of amphibian lipoxygenase on the wound closure in a scratch assay. U2-OS cells were transfected with human lipoxygenase or amphibian lipoxygenase obtained from axolotl. The reduction of in vitro wounds introduced by scratch assays was measured after 16 hours of incubation. FIG. 2a shows the wound of the control experiment, while

DETAILED DESCRIPTION OF THE PRESENT INVENTION

Figure 1:
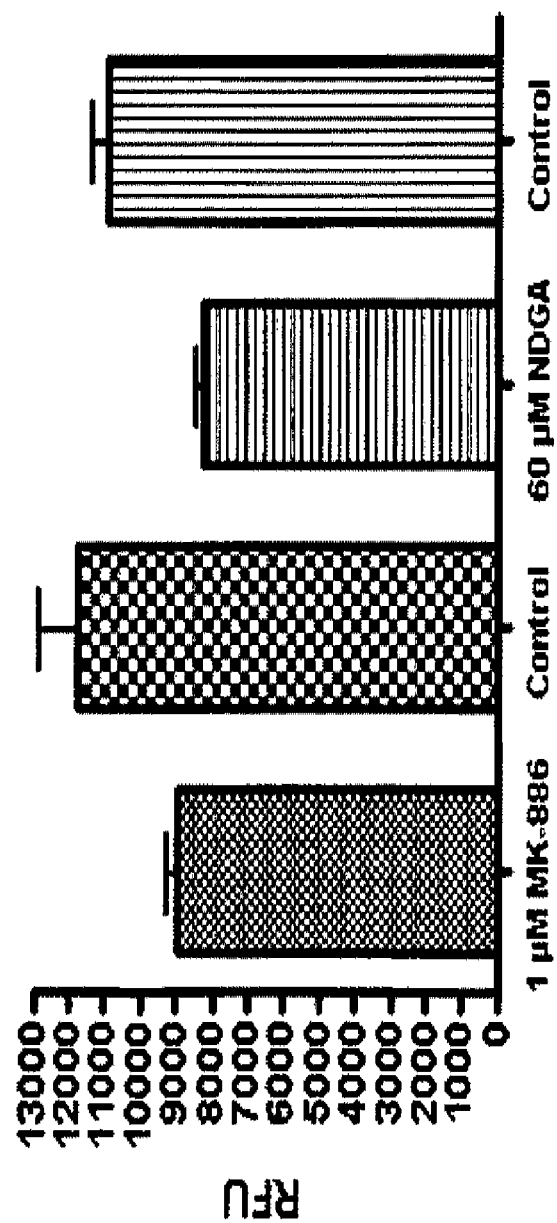
FIG. 1 demonstrates the ability of decreasing the rates of cell proliferation in amphibian epithelial cells isolated from skin biopsies when inhibiting lipoxygenase.

The present inventors isolated the enzyme lipoxygenase, namely the epidermal lipoxygenase from axolotl (AmbLOXe), Seq. ID. Nos. 1 and 2, EMBL Accession No. EU814616, and recognised that said enzyme is involved in early regenerative stages influencing epidermal migration, cell proliferation and wound closure.

Hence, in a first aspect, the present invention relates to a pharmaceutical composition containing a polypeptide of SEQ ID No. 2 having a lipoxygenase enzyme activity or functional homologues thereof having a sequence similarity of at least 50% to the sequence of SEQ ID No. 2 whereby said homologues have lipoxygenase enzyme activity, or nucleic acids encoding said polypeptides.

As used herein, the terms "polypeptide", "peptide" and "protein" are used interchangeably herein to refer to a polymer of amino acid residues. Polypeptides refers to both short chains, which are referred to as peptides, polypeptides or oligomers, and to longer chains generally referred to as proteins. The terms also apply to amino acid polymers in which one or more amino acid residues is an artificial chemical analogue of a corresponding natural occurring amino acid, as well as to naturally occurring amino acid polymers. Polypeptides include those modified either by natural processes, such as processing and other post-translational modifications, but also by chemical modification techniques. Such modifications are well described in basic texts and in more detailed monographs and they are well-known of the skilled in the art. It will be appreciated that the same type of modification will be present in the same or varying degree at several sites in a given polypeptide. Preferably, the polypeptide comprises for example 10 or more amino acids, like 20 or more amino acids, in particular 30 or more amino acids, like 50, 70 or at least 100 amino acids.

As used herein, the expression "functional derivative" or "functional homologue" refers to a protein/peptide/polypeptide sequence that possesses a functional biological activity that is substantially similar to the biological activity of the whole protein/peptide/polypeptide sequence. Namely, the functional derivative displays a lipoxygenase enzyme activity essentially as the polypeptide of SEQ ID No. 2. That is, the functional derivative refers to a polypeptide having lipoxygenase activity able to catalyse the oxidation of unsaturated fatty acids with oxygen resulting in a fatty acid hydroperoxide. Said functional derivative or functional homologue of the polypeptide having lipoxygenase activity may or may not contain post-translational modifications, such as carbohydrates.

The expression "lipoxygenase enzyme activity" refers to the catalytic activity of a family of iron containing enzymes that catalyses the oxygenation of poly unsaturated fatty acids in liquids containing a cis,cis-1,4-pentadiene structure (EC1.13.11.). For example, the lipoxygenase enzyme activity results in arachidonate metabolites, such as hydroxyeicosatetraenoic acids (HETEs) e.g. (5Z,8Z,10E,12S,14Z)-12-hydroperoxyeicosa-5,8,10,14-tetraenoate, (5Z,8Z,11Z,13E,15S)-15-hydroxyperoxyeicosa-5,8,11,13-tetraenoate, (5Z,8R,9E,11Z,14Z)-8-hydroxyperoxyeicosa-5,9,11,14-tetraenoate, and the like.

The term "nucleic acid" as used in the present invention refers to DNA (deoxynucleic acid) or RNA (ribonucleic acid) and their single or double strained polymers (polynucleotides). The term "DNA" includes cDNA. Unless limited, the term includes those nucleic acids having single structure of the reference nucleic acid and those natural nucleic acid analogues already known and metabolized in the similar way as natural nucleic acids.

The sequence similarity as used herein refers to expressing sequence identity compared to the sequence shown in SEQ ID No. 2. Sequence similarity is identical with the term "sequence homology". Preferably, the sequence similarity or homology is at least 50%, for example 60%, 70%, 80%, 90%, more preferred at least 92%, like 95%, 96%, 97%, 98% and in particular preferred at least 99%.

One can use programs like Clustal program to compare amino acid sequences or the Blast program allowing comparing amino acid sequences and finding the optimal alignment. These programs allow calculating amino acids similarity or homology for an optimal alignment. That is, amino acid alignment in sequence "identity" and "similarity" are determined from an optimal global alignment to the two sequences being compared. The skilled person is well aware of suitable programs during similarity or homology analysis.

In a preferred embodiment, the present invention comprises the lipoxygenase enzyme of SEQ ID No. 2 which represents the epidermal lipoxygenase enzyme of axolotl.

In a further embodiment, the present invention refers to a wound dressing. Said wound dressings are particular useful for conditions of chronic ulcers where the healing process is prolonged, incomplete and proceeds in an uncoordinated manner resulting in poor anatomical and functional outcome. Clinically, wounds are categorized as acute and chronic based on the timelines of healing.

Most chronic ulcers are associated with a small number of well-defined clinical entities, particularly, chronic venous stasis, diabetes mellitus and pressure ulcers.

Normally, chronic wound are very different. For example, pressure ulcers are characterized by deep tissue necrosis with loss of muscle and fat that is disproportionately greater than the loss of overlaying skin. Today, the majority of the effort to improve rates of healing of chronic wounds have focus on the use of exogenous peptide growth factors and cell based products such as cytokines. Furthermore, other small molecules including peptide derived agents and nucleic acid molecules have been suggested. However, for most parts, these attempts have met with little notable success. Hence, the wound dressings according to the present invention are useful for the treatment of wounds, especially for the treatment of chronic, non-healing wounds. Typically, wound dressings according to the present invention are comprised of extra support matrix and the active ingredient associated with the support matrix in a non-reversible or reversible manner, a polypeptide having lipoxygenase enzyme activity of SEQ ID No. 2 or functional homologues thereof having a sequence similarity of at least 50%, like at least 70%, preferably at least 90% to the sequence of SEQ ID No. 2 or nucleic acids encoding the same.

Preferably, the lipoxygenase enzyme activity is provided in form of a sustained release form.

The wound dressing may be applied to wounds or to enhance wound healing, especially the healing of chronic wounds.

The pharmaceutical composition according to the present invention may be applied on the wound dressing to allow integration of the active ingredient of the pharmaceutical composition into the wound dressing allowing release of the pharmaceutical composition into the wound area.

That is, the pharmaceutical composition may be provided in a known form of pharmaceutical compositions allowing release of the polypeptide, peptide protein directly into the area or allowing transfection of cells surrounding the wound with nucleic acids encoding the lipoxygenase enzyme according to the present invention.

That is, the pharmaceutical composition may be present in various forms. In case of nucleic acids encoding the lipoxygenase enzyme activity, the nucleic acid may be present as naked nucleic acid molecules in form of naked DNA or may be part of an appropriate nucleic acid expression vector allowing administration of the same so that it becomes intracellular, e.g. by infection using a defective or attenuated retroviral or other viral vector. The naked DNA may be applied by direct injection or by use of a micro particle bombardment. Furthermore, the nucleic acid or polypeptide may be admixed or coated with lipids or cell surface receptors or transfecting agents or may be provided in an encapsulated form, encapsulated by polymers or encapsulated with liposomes, micro particles or micro capsules or the like. The polypeptide may comprises additional moieties allowing targeting and cellular uptake of the polypeptides, for example by linking said polypeptide to known signal sequences or ligands of cell surface receptors. Alternatively, the nucleic acid can be introduced intracellularly and incorporated with the host cell DNA for expression by homologous recombination. The form and amount of the therapeutic nucleic acid or therapeutic polypeptide envisaged for use depends on the type of disease and the severity of its desired effect, patient state, etc. and can be determined by one skilled in the art.

Of course, the pharmaceutical composition may optionally comprise pharmaceutically acceptable carrier, diluents and/or recipients.

The pharmaceutical composition may be administered with a physiologically acceptable carrier to a patient, as described herein. In a specific embodiment, the term "pharmaceutically acceptable" means approved by a regulatory agency or other generally recognized pharmacopoeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium, carbonate, etc. Examples of suitable pharmaceutical carriers are described in "Remington's Pharmaceutical Sciences" by E. W. Martin (18$^{th}$ ed., Mack Publishing Co., Easton, Pa. (1990)). Such compositions will contain a therapeutically effective amount of the aforementioned compounds, salts or solvates thereof, preferably in purified form, together with a suitable amount of carrier so as to provide the form for proper administration to the patient. The formulation should suit the mode of administration.

Typically, pharmaceutically or therapeutically acceptable carrier is a carrier medium which does not interfere with the effectiveness of the biological activity of the active ingredients and which is not toxic to the host or patient.

The term "administered" means administration of a therapeutically effective dose of the aforementioned pharmaceutical composition as defined herein to an individual. By "therapeutically effective amount" is meant a dose that produces the effects for which it is administered. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art.

In addition, the pharmaceutical composition described herein may be characterized in that the components of the pharmaceutical composition are associated and/or incorporated and/or coated to a physical particle, preferably microparticle, nanoparticle, liposome, ISCOM, copolymer and/or biological particle The administration of the pharmaceutical composition can be done in a variety of ways as discussed above, including, but not limited to, orally, subcutaneously, intravenously, intraarterial, intranodal, intramedullary, intrathecal, intraventricular, intranasally, conjunctival, intrabronchial, transdermally, intrarectally, intraperitoneally, intramuscularly, intrapulmonary, vaginally, rectally, or intraocularly.

Pharmaceutical compositions according to the present invention are particularly useful in wound healing, bone healing, in particular non-healing fractions, conditioning of tissue, conditioning of scars, in particular hypertrophic scars.

Furthermore, the pharmaceutical compositions, in particular in form of wound dressings are useful for treating chronic wounds or for conditioning wound basis for transplantation of e.g. skin. That is, the pharmaceutical compositions are useful for treating burns.

Moreover, the pharmaceutical composition or wound dressings are useful in plastic surgery for example in combination with artificial tissue for tissue reconstruction or tissue replacement, for example xenogenic artificial tissue replacement using a cellularized bovine dermis.

In addition, in transplantation surgery or implant surgery, the pharmaceutical compositions are particular useful e.g. for treating or preventing fibrotic complications.

Further, the pharmaceutical composition may be applied for augmenting or supporting treatment of traumatic defects of cutis or sub-cutis, e.g. cutis laxa or striae, due to adulated deficiencies or functional or aesthetic deficiencies. Thus, it is possible to treat wounds for rapid wound closure and a functional and aesthetically satisfactory scar.

Particularly, wound dressing consisting of or containing parts of natural or artificial polymers, e.g. fibrin, fibrinogen, and hyaluronic acid, influencing blood clotting, cell migration, cell-matrix interactions, inflammation and angiogenesis can be combined with the lipoxygenase activity.

In a further aspect, the present invention relates to the use of a polypeptide having lipoxygenase enzyme activity of SEQ ID No. 2 or functional homologues thereof having a sequence similarity of at least 50%, like at least 70%, preferably at least 90% of SEQ ID No. 2 having a lipoxygenase activity, or nucleic acid molecules encoding the same, for the in vitro generation of artificial tissue, in particular skin.

That is, the lipoxygenase enzyme may be administered to cell cultures for in vitro generation of artificial tissues, e.g. skin for later transplantation or for use as a skin model in research and development. For example, said artificial tissue transplants may be transplanted to an individual having burns and the like. Skin cells, like stem cells, epithelial cells, fibroblasts or keratinocytes may be taken from said individual and said cells may be expanded in vitro for later transplantation to the same individual. The use of the lipoxygenase enzyme according to the present invention allows to promote proliferation and development of the artificial tissue. Thus, in a further embodiment, the present invention relates to a method for the in vitro generation of artificial tissue, in particular of skin comprising the step of culturing cells, like stem cells, epithelial cells, fibroblasts or keratinocytes forming said artificial tissue in the presence of a polypeptide having lipoxygenase enzyme activity of SEQ ID No. 2 or functional homologues thereof having a sequence similarity of at least 50%, like at least 70%, in particular at least 90% of the sequence of SEQ ID No. 2 having a lipoxygenase activity, or nucleic acids encoding the same.

The method includes transfection of the cells with the lipoxygenase either as a polypeptide or in form of nucleic acids, e.g. using an expression vector. Said transfection may be a transient or may be a stable transfection.

Preferably, the cells cultured in the presence of the polypeptide or acid molecules according to the present invention are autologous keratinocytes of an individual which will receive the artificial tissue later. Particularly, said method comprises the step of culturing autologous keratinocytes used as a transplant for individuals suffering from burn injuries. Alternatively, stem cells may be used for the generation of the artificial tissue.

Moreover, the present invention relates to a method for identifying modulators of wound healing, scarring, regeneration, carcinogenesis comprising the step of determining the ability of candidate agents for altering the activity of a polypeptide having lipoxygenase enzyme activity of SEQ ID No. 2 or functional homologues thereof having a sequence similarity of at least 50%, like at least 70%, in particular at least 90% of the sequence of SEQ ID No. 2 having a lipoxygenase activity.

The lipoxygenase enzyme of axolotl of SEQ ID No. 1 and SEQ ID No. 2 representing the epidermal lipoxygenase (full length AmbLOXe) was found to be involved in early regenerative status influencing epidermal migration, cell proliferation and wound closure. The full length AmbLOXe of SEQ ID No. 1 was amplified by RACE technique based on a sequence fragment identified in the salamander genome project. The biological function of AmbLOXe as well as promoter activities were examined in cell culture systems and in vivo. As shown below in the examples, inhibiting the lipoxygenase results in a 24% decrease in cell proliferation and impaired migratory activity. Furthermore, it has been surprisingly found that the lipoxygenase obtained from axolotl allow a more rapid wound closure compared to the human analogue. Thus, the lipoxygenase of axolotl of SEQ ID No. 2 or functional equivalents thereof having essentially the same enzymatic activity will allow improved wound healing.

In a further aspect, the present invention relates to a cosmetical composition containing the polypeptide having lipoxygenase enzyme activity of SEQ ID No. 2 or functional homologues thereof having a sequence similarity of at least 50%, like at least 70%, preferably at least 90% of SEQ ID No. 2 having a lipoxygenase activity, or nucleic acid molecules encoding the same.

The cosmetical composition may be adapted to allow topical administration, in particular in form of a cream, salve, lotion or ointment.

The cosmetical composition may be used for conditioning of scars. The cosmetical composition is particular useful for the use in conditioning of scars, cicatrice, degenerative occurrences like wrinkles and photodamage of the skin.

Finally, the present invention provides a method using an animal model for identifying modulators of wound healing including the step of applying the polypeptide having lipoxygenase enzyme activity as described herein and candidate agents for altering the activity of said enzyme in order to identify modulators of wound healing, scarring, regeneration, carcinogenesis etc. Further, metabolites of the lipoxygenase enzyme activity, that is, e.g. lipoxygenase derived arachidonate metabolites, such as hydroxyeicosatetraenoic acids, may be used to improve wound healing, scarring, regeneration of tissue, carcinogenesis etc.

The present invention will be illustrated in more detail in the examples below without to be construed to be limited thereto.

EXAMPLES

Example 1

Inhibition of Lipoxygenases Leads to Decreasing Rates of Cell Proliferation

In order to investigate the influence of endogenous lipoxygenase activity on the migration and proliferation of epithelial Axolotl cells, skin biopsies with 2 mm diameter were taken form Axolotl tail skin. The skin biopsies were placed in cell culture dishes coated with bovine collagen I to allow for cell migration and proliferation in an in vitro wound healing model.

The wound healing is observable by marges of epithelial cell growing from borders of the skin biopsies. The proliferation rates were determined by addition of Celltiter blue (Promega), an assay for detection of metabolic activity as an indirect measurement of cell proliferation based on Resazurin/Resofurin. Two known lipoxygenase inhibitors for the human lipoxygenase were used to examine the effect of lipoxygenase activity on cell proliferation (1 µM MK-886 and 60 µM NDGA, respectively). Epithelial cell proliferation was significantly reduced when the cells were treated with lipoxygenase inhibitors, see FIG. 1.

That is, the plates were incubated for two days to ensure proliferation of epidermal cells. Then, the number of metabolizing cells was determined by Resozuran-Resofurin exchange (Celltiter blue, Promega, Madison, USA). 2 µl Resozuran solution was added to each well for two hours and the fluorescence was read in a multiplate reader at 520 nm. The detected fluorescence was expressed in relative fluorescent units (RFU), means and standard deviation were calculated from triplicates with Microsoft Excel and tested for statistical significance using student's T-test. Experiments were repeated at three independent times to ensure reproducibility.

Example 2

Scratch-Assay for Determining Ability of Wound Closure

To compare the effect of epidermal lipoxygenase of human and Axolotl origin, a human cell line, U2-OS was transfected with expression plasmids encoding for the two types of lipoxygenase (pAmbLOXe, phuLOX) in combination with a vector encoding for GFP (pEGFP-C3, Clontech) as a reporter for transfection efficiency. Controls were transfected with empty vector and pEGFP-C3.

The coding sequence of AmbLOXe was subcloned in frame into the mammalian expression vector pTriEx-1 (Novagen). Plasmids were purified from transformed DH5α using the GenElute plasmid purification Kit (Sigma). Human osteosarcoma cells U2-OS or human spontaneously immortalized keratinocyte cells HaCaT (ATCC) were seeded into 100 mm cell culture dishes and grown over night to 40-50% confluence. Cells were transiently transfected with Fugene6 (Roche, Mannheim, Germany) following the instructions of the manufacturer. Briefly, 18 µl of the reagent were diluted with 600 µl serum-free medium and incubated at room temperature. After 5 min 6 µg of a 1:1 mixture of pTriEx-AmbLOXe and pEGFP-C3 (Clontech), which encodes Green Fluorescent Protein (GFP), were supplemented and incubated for additional 15 min. The transfection complex was added to the cell dishes in a dropwise manner. Cells were incubated for 24 hours before being analyzed for transfection efficiency by detection of GFP positive cells in a flow cytometer (FC-500, Beckman-Coulter, Fullerton, Calif., USA). Only cell populations were used in which about 25% GFP positive cells (U2-OS) or 12% GFP positive cells (HaCaT) could be detected. The cells were seeded into a six well plate until they reached confluence. The monolayer was then wounded with a disposable plastic pipet tip (10 µl-100 µl volume). The cells ere incubated in DMEM High Glucose (Biochrom, Berlin, Germany) supplemented with 10% FCS). The scratches were documented by microphotography and incubated for 16 hours. Then the scratches were again photographed and the remaining areas were measured using CellD (Olympus) software program. All experiments were carried out in quadruplicates and repeated at four independent times. Means and standard deviation were calculated and tested for statistical significance with ANOVA followed by Bonferroni's posthoc test.

Figure 2A:
Figure 2C:
Figure 2B:
FIG. 2b shows the results of cells expressing the human lipoxygenase. As can be ascertained from FIG. 2b the wound closure has not finished yet. In contrast, in cells transfected with the lipoxygenase obtained from axolotl, wound closure was substantially completed after 16 hours incubation.
Figure 3:
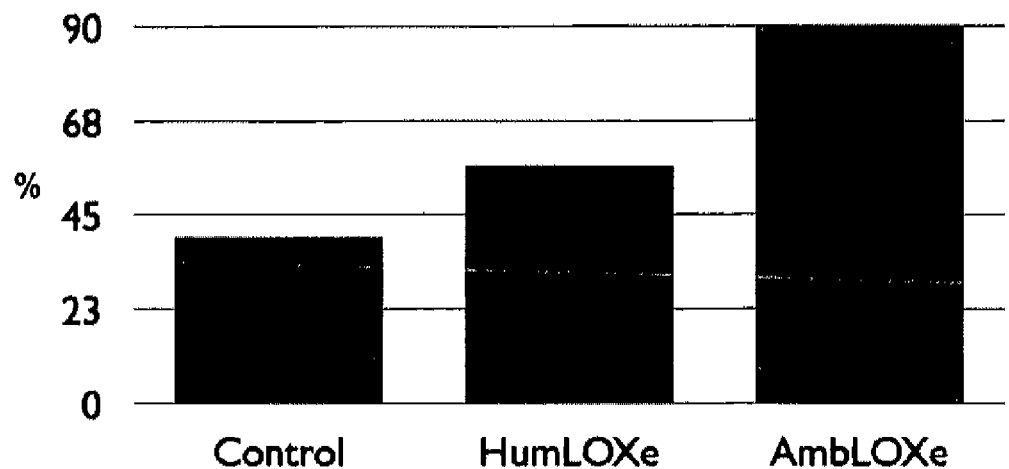
FIG. 3 provides a diagram demonstrating the reduction of a wound width in % in U2-OS cells transfected with a) control vector, b) a vector containing the human lipoxygenase and c) vector containing the lipoxygenase obtained from axolotl. The superior effect of lipoxygenase obtained from axolotl of SEQ ID No. 2 is demonstrated.
Figure 4:
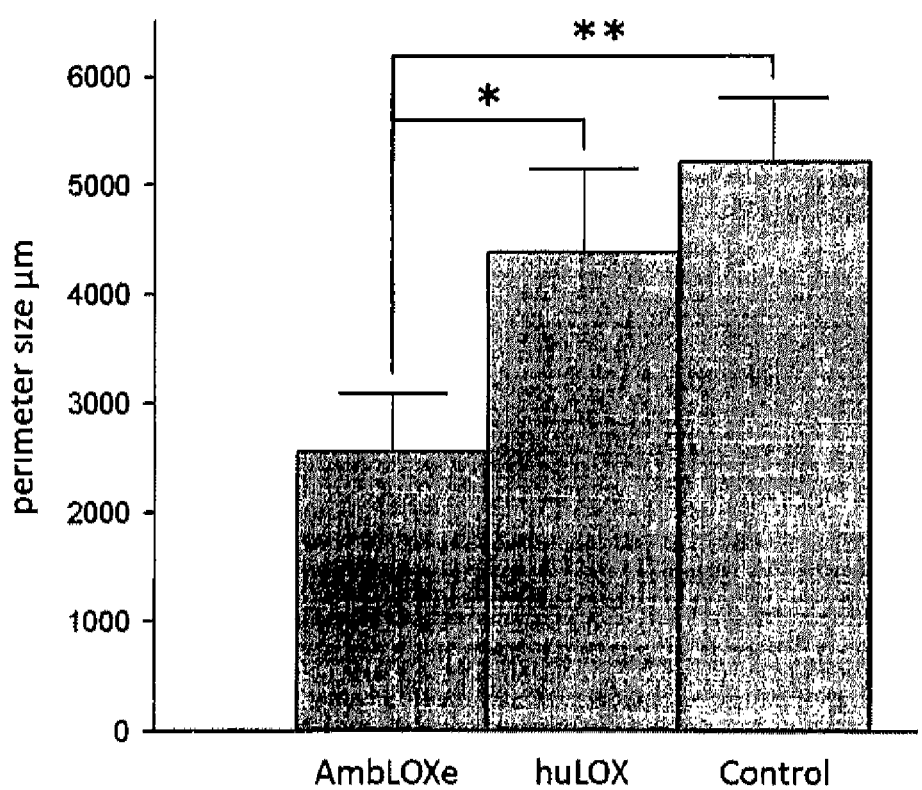
FIG. 4 demonstrates the results of transient amphibian lipoxygenase (AmbLOXe) transfection of a human keratinocyte cell line HaCaT. Shown is the cell migration in an in vitro scratch assay. That is, in an in vitro scratch assay, non-regenerated monolayers were measured and the numbers depicted as a perimeter size in μm. They are given in means (n=4) and standard deviation ($p<0.05$; $p<0.01$).

Cell populations containing cells expressing AmbLOXe showed a scratch width reduction of 89.94% while cell populations with cells expressing huLOX reduced to 56.75% and cells transfected with empty vectors (control) to 39.85%, see FIGS. 2 and 3 as well as FIG. 4 for HaCat cells.

Transfection of Human Cell Lines with AmbLOXe Enhances Cellular Migration

A cDNA fragment coding for full-length AmbLOXe was cloned in frame into the mammalian expression vector pTriEx-1 and transfected together with an expression plasmid for EGFP into the U2-OS cell line to evaluate a possible influence of AmbLOXe expression in a mammalian model system. Only cell populations with a transfection efficiency of about 25% (U2-OS), respectively 12% (HaCaT) were used for all assays and seeded to confluent monolayers which subsequently were wounded with scratches.

The remaining scratch areas photographed after 16 hours incubation were used to determine the influence of AmbLOXe expression on mammalian cell migration. While no AmbLOXe expression could be observed in U2-OS cell populations transfected with an empty vector, and in U2-OS cell populations transfected with huLOX, AmbLOXe expression was detected in U2-OS cell populations transfected with AmbLOXe encoding plasmids. A perimeter size reduction to a mean value of 24806.26 µm in the cell populations transfected with an empty vector was found; while cell populations containing AmbLOXe expressing cells and cell populations containing cells expressing human 12R LOX reduced the photographed scratch area to mean values of 517.46 µm and 2086.86 µm, respectively.

In order to determine the influence of lipoxygenase inhibitor on the transiently transfected cell populations, cells transfected with empty vector (control) and scratched cell monolayers transfected with vectors containing human 12R LOX and AmbLOXe, respectively, received an overnight treatment with NHGA. While there was no significant differences in the migration behaviour of empty vector transfected cells and cells expressing huLOX compared to the solvent treated monolayers, solvent treated cell populations expressing AmbLOXe reduced the measured wound scratch to a mean value of 3388.99 µm, while cultures treated with NHGA reduced the scratch area to a mean value of 4428.33 µm.

To investigate the influence on the migration behaviour of epithelial cells, a series of experiments with the spontaneously immortalized keratinocyte cell line HaCaT were performed. Cells were transfected with vectors encoding for AmbLOXe, huLOX and empty vector as described above.

As described for the transfected U2-OS populations cellular migration was determined in HaCaT monolayer scratch assays. After a 16 hours incubation the remaining scratch perimeter size was significantly smaller in HaCaT populations transfected with AmbLOXe encoding vector compared to the empty vector transfected cell populations (p=0.0035), and huLOX transfected populations (p=0.028).

Of note, it is identified that the treatment of MK-886 had an equal effect on the Axolotl epithelial cells than it is described for NDGA. MK-886 is an inhibitor for lipoxygenase 5 without exerting an effect on lipoxygenase 15, which is usually expressed in blood monocytes and eosinophiles. This is the first time demonstrating the inhibitory effect of MK-886 on epidermis-type lipoxygenases.

Example 3

Animal Model Demonstrating Effectiveness of Lipoxygenase Obtained from Axolotl The following experiment demonstrates the effectiveness of lipoxygenase obtained from Axolotl compared to human lipoxygenase for wound closure and wound healing. That is, murine embryonic fibroblasts were seeded in cell culture dishes to 50% confluence and were transfected with expression plasmids encoding two different types of lipoxygenase (pAmbLOXe, phuLOX), an empty vector was used as control. After 24 hours, the cells were washed and trypsinated. Cells in an amount of 100,000 cells/ml in PBS were resuspended and 200 μl cell suspension was injected into area adjacent to a wound of a full thickness skin wound. Said full thickness skin wound was prepared in advance using mice (C57/BR6 female) where the back was shaved and the skin was disinfected. Thereafter, a full thickness skin wound was set using a 8 mm biopsy punch, resulting in a 50 $mm^2$ defect. A control group was prepared not treated with any cell suspension. After day 3 and day 7 a photo was taken from the wound and the reduction of wound size was measured and determined statistically.

Figure 5:
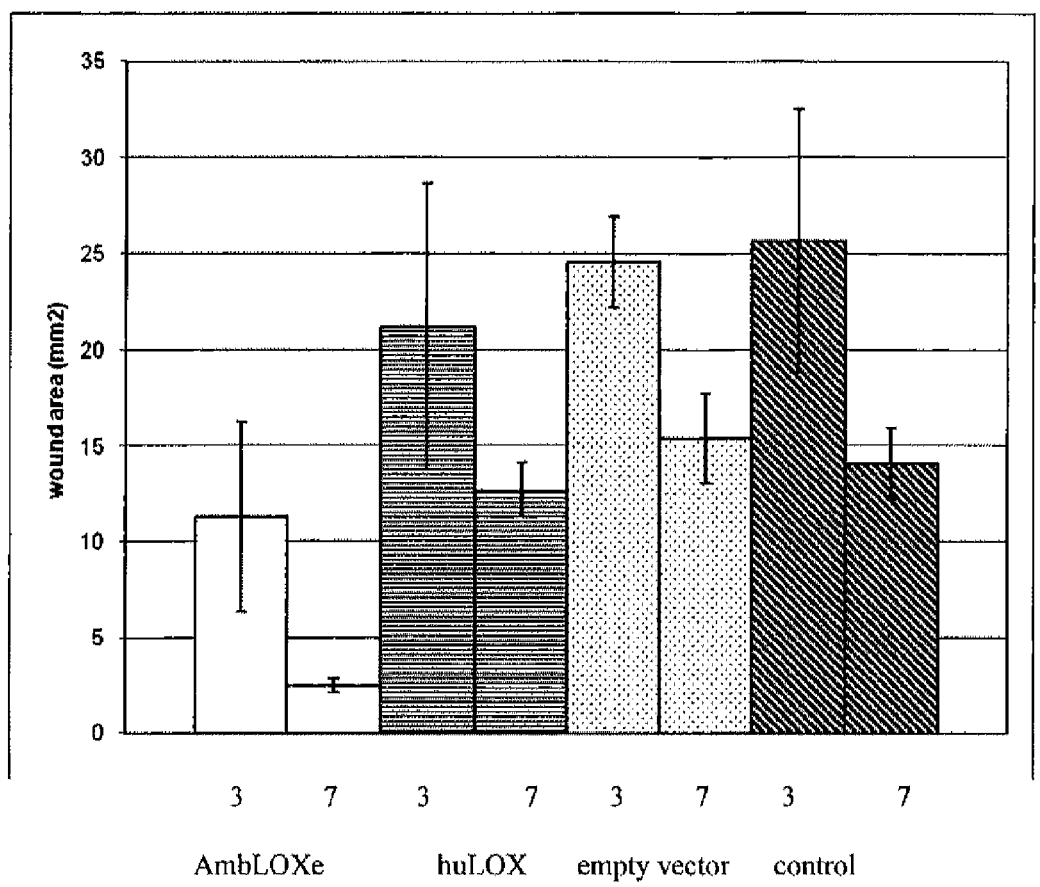
FIG. 5 shows the effect of amphibian lipoxygenase on the wound closure in an animal model. Mice having a full thickness skin wound were treated either with murine embryonic fibroplasts transfected with Axolotl lipoxygenase, human lipoxygenase or empty vector. The wound closure was determined after day 3 and day 7, respectively. As it can be ascertain from FIG. 5 wound closure has not finished yet. However, a significant reduction of wound closure can be observed with the amphibian lipoxygenase obtained from Axolotl while the human lipoxygenase is comparable with the control groups.

As shown in FIG. 5, the wound size of the axolotl lipoxygenase group was reduced dramatically on day 3 and, in particular, day 7 compared to the human lipoxygenase treated group and the group treated with cells transfected with the empty vector as well as the control not treated with any cells. In particular, a significant reduction in wound closure can be observed with the lipoxygenase of Axolotl only.

Hence, the beneficial effect of using the lipoxygenase according to the present invention is demonstrated in this animal model.

The invention claimed is:

1. A composition containing a vector comprising a heterologous nucleic acid molecule encoding the recombinant polypeptide of SEQ ID NO: 2 having lipoxygenase enzyme activity.

2. A wound dressing containing
   a substrate containing polymers; and, positioned on or associated with said substrate, a composition comprising
   i) the polypeptide of SEQ ID No. 2 having lipoxygenase enzyme activity, or
   ii) the nucleic acid molecule encoding said polypeptide of SEQ ID No. 2.

3. The wound dressing according to claim 2 wherein said polypeptide of SEQ ID No. 2 is present in a sustained-release form.

4. The composition of claim 1, wherein said nucleic acid molecule encoding said polypeptide of SEQ ID No. 2 is SEQ ID No. 1.

5. The wound dressing of claim 2, wherein said nucleic acid molecule encoding said polypeptide of SEQ ID No. 2 is SEQ ID No. 1.

6. The composition of claim 1 wherein said composition is formulated for cosmetic applications.

7. The composition of claim 1 wherein said composition is formulated for pharmaceutical applications.

* * * * *

SEQUENCE LISTING

```
<160> NUMBER OF SEQ ID NOS: 2

<210> SEQ ID NO 1
<211> LENGTH: 2376
<212> TYPE: DNA
<213> ORGANISM: Ambystoma mexicanum
<220> FEATURE:
<221> NAME/KEY: CDS
<222> LOCATION: (140)..(2011)

<400> SEQUENCE: 1
gacagtagcg ctgccgagtg acaacggtgc acagctcaag ccccggtgca gtggcatgga      60
atttgctctg ttttgaaggg gaaaccactg cgttcctgag aaactggtgc tttctgaacc     120
gcttcagacg tcgaagcaa atg gtg gat gag tac cgc atc aaa gag gac cgt     172
                    Met Val Asp Glu Tyr Arg Ile Lys Glu Asp Arg
                     1               5                  10 gat ctg ggg gaa atc ctg ctc atc cgt ctc cac aag ggg ccc ttc tcc     220
Asp Leu Gly Glu Ile Leu Leu Ile Arg Leu His Lys Gly Pro Phe Ser
         15                  20                  25 atc ttc cca gag gac aac tgg tac tgc atg tat gta act gtg acg tcc     268
Ile Phe Pro Glu Asp Asn Trp Tyr Cys Met Tyr Val Thr Val Thr Ser
     30                  35                  40 cct ggc gga gtg atc tac cac ttc ccc tgt tac cgc tgg atc gaa ggc     316
Pro Gly Gly Val Ile Tyr His Phe Pro Cys Tyr Arg Trp Ile Glu Gly
 45                  50                  55 tac cca aca gtg gag ctc gca gaa ggg aca gct atg ctg agt tct gca     364
Tyr Pro Thr Val Glu Leu Ala Glu Gly Thr Ala Met Leu Ser Ser Ala
 60                  65                  70                  75 agc aat ctt cac gtg aca cta aaa aaa cag cga gag agt gat ctg gaa     412
Ser Asn Leu His Val Thr Leu Lys Lys Gln Arg Glu Ser Asp Leu Glu
                 80                  85                  90 cag aga aga aag gtc tac agg tgg aaa gtc tac cac ccc agt ttt ccc     460
Gln Arg Arg Lys Val Tyr Arg Trp Lys Val Tyr His Pro Ser Phe Pro
             95                 100                 105 aag tgc att gat gtg gcc aac aac gat gag ctg gac aaa gac gcc aag     508
Lys Cys Ile Asp Val Ala Asn Asn Asp Glu Leu Asp Lys Asp Ala Lys
        110                 115                 120
```

```
tac tcc atc acg aaa aca gtc cac ttt gtt atc aac aag aat gtt tca      556
Tyr Ser Ile Thr Lys Thr Val His Phe Val Ile Asn Lys Asn Val Ser
        125                 130                 135 aac atc gcg ata aaa ctg aaa ggc ttt gac gga cga cag gaa tcc tgg      604
Asn Ile Ala Ile Lys Leu Lys Gly Phe Asp Gly Arg Gln Glu Ser Trp
140                 145                 150                 155 aaa tcc ttt gat gaa ctc aag agg gtt tat tgg acc cta aaa act gcg      652
Lys Ser Phe Asp Glu Leu Lys Arg Val Tyr Trp Thr Leu Lys Thr Ala
                160                 165                 170 aaa tca gag tat gtc tct cac cac tgg aaa gaa gat gca ttt ttt ggg      700
Lys Ser Glu Tyr Val Ser His His Trp Lys Glu Asp Ala Phe Phe Gly
            175                 180                 185 tac cag tac ctg aat ggc cct gac ccc aca ctg atc aag agg tgt aac      748
Tyr Gln Tyr Leu Asn Gly Pro Asp Pro Thr Leu Ile Lys Arg Cys Asn
        190                 195                 200 aaa att cct ggc aac ttc cca gtc aca gat gag atg gtg tcc tac agt      796
Lys Ile Pro Gly Asn Phe Pro Val Thr Asp Glu Met Val Ser Tyr Ser
205                 210                 215 ctg gga gct tcg aca agc ctt gag aag gag ctg cag aaa gga aac att      844
Leu Gly Ala Ser Thr Ser Leu Glu Lys Glu Leu Gln Lys Gly Asn Ile
220                 225                 230                 235 tac att gtg gat cac aag atg atg gaa gga ctt cgt gca aat gtg cta      892
Tyr Ile Val Asp His Lys Met Met Glu Gly Leu Arg Ala Asn Val Leu
                240                 245                 250 aat ggc aag cag cag tac atg gct gct cct ttg tgt ctc ttc tac cgc      940
Asn Gly Lys Gln Gln Tyr Met Ala Ala Pro Leu Cys Leu Phe Tyr Arg
            255                 260                 265 aca cct aag gat gag gtt atc cca ttg gct atc cag tta aat cag act      988
Thr Pro Lys Asp Glu Val Ile Pro Leu Ala Ile Gln Leu Asn Gln Thr
        270                 275                 280 ccg ggt tca gag act ccc ctc ttc ctg cca agc gac aat gag tgg gat     1036
Pro Gly Ser Glu Thr Pro Leu Phe Leu Pro Ser Asp Asn Glu Trp Asp
285                 290                 295 tgg ata ctc gct aag att tgg gta cgg tct aca tcc ttt gct ttc cac     1084
Trp Ile Leu Ala Lys Ile Trp Val Arg Ser Thr Ser Phe Ala Phe His
300                 305                 310                 315 cag gct gtc tct cac ttt ctg cgg acg cac gtc ttt gca gag gtg ttt     1132
Gln Ala Val Ser His Phe Leu Arg Thr His Val Phe Ala Glu Val Phe
                320                 325                 330 tgc ttg gcc acc ttg cgg cag cta cca atg gct cac cca cta tac aag     1180
Cys Leu Ala Thr Leu Arg Gln Leu Pro Met Ala His Pro Leu Tyr Lys
            335                 340                 345 ctt ctg gtt ccc cac cta cgc tac act tta cag atc aat gtg ctt gcg     1228
Leu Leu Val Pro His Leu Arg Tyr Thr Leu Gln Ile Asn Val Leu Ala
        350                 355                 360 aga gag cgt cta att gga ccg gga gga gcc ttc gat aag aac acc gca     1276
Arg Glu Arg Leu Ile Gly Pro Gly Gly Ala Phe Asp Lys Asn Thr Ala
365                 370                 375 gtt gga atc gcc ggt att gct gaa ctg ata aag aga gac atg gaa act     1324
Val Gly Ile Ala Gly Ile Ala Glu Leu Ile Lys Arg Asp Met Glu Thr
380                 385                 390                 395 ctg aaa tac tct act ctc tgt ttg cct gaa aat ctc cag tcc cgt gag     1372
Leu Lys Tyr Ser Thr Leu Cys Leu Pro Glu Asn Leu Gln Ser Arg Glu
                400                 405                 410 gtc gag tcg ctg cct cat ttt tac tac cga gat gat gga atg aaa att     1420
Val Glu Ser Leu Pro His Phe Tyr Tyr Arg Asp Asp Gly Met Lys Ile
            415                 420                 425 tgg ttg gcc atc gag agt tat gtg tca ggc att gtt gac tat tac tat     1468
Trp Leu Ala Ile Glu Ser Tyr Val Ser Gly Ile Val Asp Tyr Tyr Tyr
        430                 435                 440
```

```
aag agt gag gag agc atc cag aag gac cct gag ctg cag gcc tgg gtg      1516
Lys Ser Glu Glu Ser Ile Gln Lys Asp Pro Glu Leu Gln Ala Trp Val
        445                 450                 455 gcc gag atc ttc aaa gaa ggt ttc ttg gag aga aaa tcc tca ggc atc      1564
Ala Glu Ile Phe Lys Glu Gly Phe Leu Glu Arg Lys Ser Ser Gly Ile
460                 465                 470                 475 cct tct tct ctg gag acc cgc gtg gag ctc att aag tat ctg acc atg      1612
Pro Ser Ser Leu Glu Thr Arg Val Glu Leu Ile Lys Tyr Leu Thr Met
                480                 485                 490 gtg atc ttc aca tgc tca gcc gag cat gct gct gtc aac agt ggg cag      1660
Val Ile Phe Thr Cys Ser Ala Glu His Ala Ala Val Asn Ser Gly Gln
            495                 500                 505 ttt gat ttc ctc tcc tgg atg ccc aac ggt ccc agc aca atg cga cag      1708
Phe Asp Phe Leu Ser Trp Met Pro Asn Gly Pro Ser Thr Met Arg Gln
        510                 515                 520 cct cct ccc aag acc aag ggc ttg gca aca atg gaa agc gtc ctg gaa      1756
Pro Pro Pro Lys Thr Lys Gly Leu Ala Thr Met Glu Ser Val Leu Glu
525                 530                 535 gcc cta cct gag gtg ggc atc acc acc aac ata atg acg act gtc tgg      1804
Ala Leu Pro Glu Val Gly Ile Thr Thr Asn Ile Met Thr Thr Val Trp
540                 545                 550                 555 acc ctg agt aaa gag cct ggg gac atg aga cct ctg ggc acc tac cct      1852
Thr Leu Ser Lys Glu Pro Gly Asp Met Arg Pro Leu Gly Thr Tyr Pro
                560                 565                 570 gat gaa cat ttc acg gag gag gga ccc aaa cag tgc atc cgg gca ttc      1900
Asp Glu His Phe Thr Glu Glu Gly Pro Lys Gln Cys Ile Arg Ala Phe
            575                 580                 585 cag gaa cgt ctg tct gag ata tcc aga gag att gag cac aga aac gca      1948
Gln Glu Arg Leu Ser Glu Ile Ser Arg Glu Ile Glu His Arg Asn Ala
        590                 595                 600 tcc cta ccc atc aag tac aac tac atg aac ccc aaa gtg ata gag aac      1996
Ser Leu Pro Ile Lys Tyr Asn Tyr Met Asn Pro Lys Val Ile Glu Asn
605                 610                 615 agt gtg tcc ata taa ctgtaaataa ggagccagca acacccct gcactgccaa        2051
Ser Val Ser Ile
620 ccaaagccca tctaccatca gtaaaagcat tcctcatacc cttagatttc aataatatcc    2111 agaaagaaca tccaccccga cacccagtg tctgataacc gacacaaaag catttcatat     2171 aaagtctgat ttcaacaagc aaacagtaag aatgttccag aatgttctgg aatcaatgtg    2231 acatagccaa tgagagcatc aaccttgctg aggtaatgca cgaccttgca ggccatcagc    2291 cggaagccac tctcagtggt agaagtgtac caaaagaagt agtggaaccg taaccccaac    2351 agaggacaga gaaggtggga gcatg                                         2376

<210> SEQ ID NO 2
<211> LENGTH: 623
<212> TYPE: PRT
<213> ORGANISM: Ambystoma mexicanum

<400> SEQUENCE: 2

Met Val Asp Glu Tyr Arg Ile Lys Glu Asp Arg Asp Leu Gly Glu Ile
1               5                   10                  15

Leu Leu Ile Arg Leu His Lys Gly Pro Phe Ser Ile Phe Pro Glu Asp
                20                  25                  30

Asn Trp Tyr Cys Met Tyr Val Thr Val Thr Ser Pro Gly Gly Val Ile
            35                  40                  45

Tyr His Phe Pro Cys Tyr Arg Trp Ile Glu Gly Tyr Pro Thr Val Glu
        50                  55                  60
```

```
Leu Ala Glu Gly Thr Ala Met Leu Ser Ser Ala Ser Asn Leu His Val
65                  70                  75                  80

Thr Leu Lys Lys Gln Arg Glu Ser Asp Leu Glu Gln Arg Arg Lys Val
                85                  90                  95

Tyr Arg Trp Lys Val Tyr His Pro Ser Phe Pro Lys Cys Ile Asp Val
            100                 105                 110

Ala Asn Asn Asp Glu Leu Asp Lys Asp Ala Lys Tyr Ser Ile Thr Lys
        115                 120                 125

Thr Val His Phe Val Ile Asn Lys Asn Val Ser Asn Ile Ala Ile Lys
    130                 135                 140

Leu Lys Gly Phe Asp Gly Arg Gln Glu Ser Trp Lys Ser Phe Asp Glu
145                 150                 155                 160

Leu Lys Arg Val Tyr Trp Thr Leu Lys Thr Ala Lys Ser Glu Tyr Val
                165                 170                 175

Ser His His Trp Lys Glu Asp Ala Phe Phe Gly Tyr Gln Tyr Leu Asn
            180                 185                 190

Gly Pro Asp Pro Thr Leu Ile Lys Arg Cys Asn Lys Ile Pro Gly Asn
        195                 200                 205

Phe Pro Val Thr Asp Glu Met Val Ser Tyr Ser Leu Gly Ala Ser Thr
    210                 215                 220

Ser Leu Glu Lys Glu Leu Gln Lys Gly Asn Ile Tyr Ile Val Asp His
225                 230                 235                 240

Lys Met Met Glu Gly Leu Arg Ala Asn Val Leu Asn Gly Lys Gln Gln
                245                 250                 255

Tyr Met Ala Ala Pro Leu Cys Leu Phe Tyr Arg Thr Pro Lys Asp Glu
            260                 265                 270

Val Ile Pro Leu Ala Ile Gln Leu Asn Gln Thr Pro Gly Ser Glu Thr
        275                 280                 285

Pro Leu Phe Leu Pro Ser Asp Asn Glu Trp Asp Trp Ile Leu Ala Lys
    290                 295                 300

Ile Trp Val Arg Ser Thr Ser Phe Ala Phe His Gln Ala Val Ser His
305                 310                 315                 320

Phe Leu Arg Thr His Val Phe Ala Glu Val Phe Cys Leu Ala Thr Leu
                325                 330                 335

Arg Gln Leu Pro Met Ala His Pro Leu Tyr Lys Leu Leu Val Pro His
            340                 345                 350

Leu Arg Tyr Thr Leu Gln Ile Asn Val Leu Ala Arg Glu Arg Leu Ile
        355                 360                 365

Gly Pro Gly Gly Ala Phe Asp Lys Asn Thr Ala Val Gly Ile Ala Gly
    370                 375                 380

Ile Ala Glu Leu Ile Lys Arg Asp Met Glu Thr Leu Lys Tyr Ser Thr
385                 390                 395                 400

Leu Cys Leu Pro Glu Asn Leu Gln Ser Arg Glu Val Glu Ser Leu Pro
                405                 410                 415

His Phe Tyr Tyr Arg Asp Asp Gly Met Lys Ile Trp Leu Ala Ile Glu
            420                 425                 430

Ser Tyr Val Ser Gly Ile Val Asp Tyr Tyr Lys Ser Glu Glu Ser
        435                 440                 445

Ile Gln Lys Asp Pro Glu Leu Gln Ala Trp Val Ala Glu Ile Phe Lys
    450                 455                 460

Glu Gly Phe Leu Glu Arg Lys Ser Ser Gly Ile Pro Ser Ser Leu Glu
465                 470                 475                 480
```

-continued

```
Thr Arg Val Glu Leu Ile Lys Tyr Leu Thr Met Val Ile Phe Thr Cys
            485                 490                 495

Ser Ala Glu His Ala Ala Val Asn Ser Gly Gln Phe Asp Phe Leu Ser
            500                 505                 510

Trp Met Pro Asn Gly Pro Ser Thr Met Arg Gln Pro Pro Lys Thr
        515                 520                 525

Lys Gly Leu Ala Thr Met Glu Ser Val Leu Glu Ala Leu Pro Glu Val
        530                 535                 540

Gly Ile Thr Thr Asn Ile Met Thr Thr Val Trp Thr Leu Ser Lys Glu
545                 550                 555                 560

Pro Gly Asp Met Arg Pro Leu Gly Thr Tyr Pro Asp Glu His Phe Thr
                565                 570                 575

Glu Glu Gly Pro Lys Gln Cys Ile Arg Ala Phe Gln Glu Arg Leu Ser
            580                 585                 590

Glu Ile Ser Arg Glu Ile Glu His Arg Asn Ala Ser Leu Pro Ile Lys
        595                 600                 605

Tyr Asn Tyr Met Asn Pro Lys Val Ile Glu Asn Ser Val Ser Ile
610                 615                 620
```